United States Patent [19]

Croudace

[11] Patent Number: 4,764,298

[45] Date of Patent: Aug. 16, 1988

[54] LUBRICATION ANTI-WEAR ADDITIVE

[75] Inventor: Michael C. Croudace, Huntington Beach, Calif.

[73] Assignee: Union Oil Company of California, Los Angeles, Calif.

[21] Appl. No.: 123,134

[22] Filed: Nov. 20, 1987

Related U.S. Application Data

[62] Division of Ser. No. 832,968, Feb. 25, 1986, abandoned.

[51] Int. Cl.$^4$ ............................................. C10M 135/36
[52] U.S. Cl. ...................................... 252/47; 548/167; 548/174; 252/47.5
[58] Field of Search ................. 252/47, 47.5; 548/165, 548/167, 174

[56] References Cited

U.S. PATENT DOCUMENTS

| | | | |
|---|---|---|---|
| 1,972,918 | 9/1934 | Bunbury et al. | 548/165 |
| 2,010,059 | 8/1935 | Coleman | 548/165 |
| 2,719,827 | 10/1955 | Lowe | 252/47 |
| 2,765,289 | 10/1956 | Fields et al. | 252/47 |
| 4,589,991 | 5/1986 | Ryer et al. | 252/47 |

*Primary Examiner*—Jacqueline V. Howard
*Attorney, Agent, or Firm*—Arthur E. Oaks; Gregory F. Wirzbicki; Dean Sandford

[57] ABSTRACT

An extreme pressure anti-wear additive soluble in lubricating oils is provided wherein the additive comprises the reaction product of a 2-mercaptobenzothiazole with (1) an aldehyde or ketone, preferably having between 1 and 10 carbon atoms, and (2) ammonia or an amine, preferably an amine containing between 8 and 40 carbon atoms. The reaction product formed is an ashless, metals-free, extreme pressure agent soluble in lubricating oils.

30 Claims, No Drawings

LUBRICATION ANTI-WEAR ADDITIVE

This application is a division of application Ser. No. 832,968, filed 02/25/86, abandoned.

BACKGROUND OF THE INVENTION

The present invention relates to an anti-wear additive for lubricating compositions and specifically to an extreme pressure, anti-wear additive.

Lubricating compositions reduce friction and reduce or prevent destructive contact between moving metal surfaces as long as a lubricating film is maintained between the moving surfaces. This particular type of lubrication is referred to as hydrodynamic lubrication.

Some anti-wear additives enhance the hydrodynamic lubrication of motor oils and the like. However, when the pressure and/or rubbing speeds between the moving metal surfaces increase, the lubricating film is forced out from between the moving metal surfaces. This results in metal-to-metal contact and wear. Lubrication under these extreme pressure conditions requires an additive that is adsorbed by or reacts with the metal to form an adherent protective film on the metal. This type of lubrication is needed under conditions called boundary lubrication, and additives enhancing this type of lubrication are known as "extreme pressure, anti-wear additives."

Many extreme pressure, anti-wear additives are known. The most commercially used additives are phosphorus-containing compounds, such as zinc dialkyldithiophosphates. While these phosphorus-containing compounds provide a high degree of boundary lubrication, there is a move away from this type of additive, especially for use in internal combustion engines. It is believed that oxidation products of phosphorus formed during combustion are carried by the exhaust gases into emission control catalysts where they reduce the life of the catalyst.

To replace phosphorus-containing compounds, various other types of extreme pressure, anti-wear additives have been used, such as the boron-containing compounds disclosed in U.S. Pat. Nos. 2,975,135, 3,347,793, 3,356,707, 3,509,054, and 4,115,286. These boron-containing compounds provide some degree of boundary lubrication, but they produce an ash upon combustion that can poison or plug emission control catalysts. Other additives of similar or superior properties to the dialkyldithiophosphates are still being sought, and particularly those which will not leave an ash residue to poison or otherwise interfere with automotive emission control catalysts.

SUMMARY OF THE PRESENT INVENTION

The present invention resides in an extreme pressure, anti-wear additive comprising the reaction product of 2-mercaptobenzothiazole with (1) a carbonyl-containing compound selected from the group consisting of aldehydes and ketones, preferably containing between 1 and 10 carbon atoms, and (2) ammonia or an amine, preferably an amine containing between 8 and 40 carbon atoms.

Preferably, the anti-wear additive of the invention is a reaction product of 2-mercaptobenzothiazole, an aldehyde or ketone, and an amine such that the reaction product comprises a compound having the following general formula:

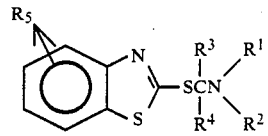

wherein $R_1$, $R_2$, $R_3$, $R_4$, and $R_5$ are independently selected from the group consisting of hydrogen and organic radicals.

Also provided is a method for enhancing the extreme pressure, anti-wear characteristics of an oleaginous lubricating composition comprising admixing into the lubricating composition an extreme pressure, anti-wear enhancing amount of the additive provided herein, provided further that $R^3$ and $R^4$ may also be chlorine or bromine.

DETAILED DESCRIPTION OF THE INVENTION

In the practice of this invention, an increase in the extreme pressure, anti-wear properties of an oleaginous material, such as a lubricating oil or grease, typically used to lubricate contact between moving metal surfaces, is accomplished by admixing into such oleaginous material a metals-free and non-ash-forming additive comprising a reaction product of (1) 2-mercaptobenzothiazole, (2) an aldehyde or ketone, and (3) a substituted or unsubstituted amine. The 2-mercaptobenzothiazole reaction products of this invention may be difficult to dissolve in the desired oleaginous material. For this reason, the aldehydes or ketones and amines are selected such that when reacted with 2-mercaptobenzothiazole the product is soluble in the oleaginous material.

In one embodiment of the invention, the anti-wear additive of the invention is the ashless and metals-free reaction product of 2-mercaptobenzothiazole, an aldehyde or ketone, and a substituted or unsubstituted amine having the following general formula:

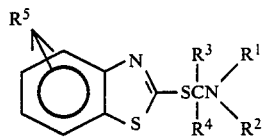

wherein $R^1$, $R^2$, $R^3$, $R^4$, and $R^5$ are independently selected from the group consisting of hydrogen and organic radicals. As used herein, an "organic radical" is one which contains at least one carbon atom. And the term "metals" as used herein is intended to include metals, semi-metals, and metalloids, all of which may be bonded ionically, covalently, or associatively.

In yet another embodiment, $R^1$ and $R^2$ are the same or different radicals selected from the group consisting of hydrogen and metals-free, substituted or unsubstituted alkyl, aryl, arylalkyl, alkyloxy, aryloxy, arylalkyloxy, alkenyl, alkenyloxy, alkynyl, alkynyloxy, arylalkenyl, and cyclic hydrocarbon radicals, and hetero-atom-substituted hydrocarbyl radicals wherein the hetero-atoms are selected from the group consisting of oxygen, sulfur, and nitrogen atoms; and $R^3$ and $R^4$ are the same or different radicals selected from the group consisting of halogen or hydrogen and metals-free, substituted or unsubstituted alkyl, aryl, arylalkyl, alkyloxy, aryloxy, arylalkyloxy, alkenyl, alkenyloxy, alkynyl, alkynyloxy, arylalkenyl, and cyclic hydrocarbon radicals, and hetero-atom-substituted hydrocarbyl radicals wherein the hetero-atoms are selected from the group consisting of oxygen, sulfur, and nitrogen atoms. $R^1$, $R^2$, $R^3$, and $R^4$ are selected so that the reaction product is soluble in the oleaginous material in which it is to serve as the extreme pressure, anti-wear additive.

The present invention further resides in a method of enhancing the extreme pressure, anti-wear characteristics of a lubrication composition comprising an oleaginous material, such as a lubricating oil or grease, by dissolving into the composition a sufficient amount of an ashless and metals-free reaction product of 2-mercaptobenzothiazole, an aldehyde or ketone, and ammonia or an amine, one such reaction product being a di-substituted aminomethylene derivative of 2-mercaptobenzothiazole. The invention also resides in the resulting lubricating composition.

DESCRIPTION OF THE PREFERRED EMBODIMENTS

Among the di-substituted aminomethylene derivatives of 2-mercaptobenzothiazole suitable herein for enhancing the extreme pressure, anti-wear properties of a lubricant are derivatives produced from 2-mercaptobenzothiazole by reaction with an aldehyde or ketone and a primary or secondary aliphatic or alicyclic amine in a mole ratio of 1:1:1. The product is formed by reaction performed at a temperature in the range from about 25° C. to about 150° C. The total reaction time may range from about 0.5 hour to about 40 hours, and the reaction may be carried out in the presence or absence of a suitable solvent. Examples of suitable solvents are dioxane, hexane, dimethyl ether, diethyl ether or toluene.

The reaction may be carried out by either: (a) mixing all three reactants together; (b) reacting the aldehyde with the amine and subsequently reacting the thiazole with the product; or (c) reacting the aldehyde with the thiazole and subsequently reacting the amine with the product. At the completion of the reaction, both the solvent and the water-of-formation are typically removed by suitable methods, such as by stripping under vacuum. Preferably, the water-of-formation is distilled off through an azeotrope trap during the progress of the reaction.

Aldehydes and ketones which may be employed in the practice of the present invention are any of the $C_1$ to $C_{20}$, preferably $C_1$ to $C_{10}$, aliphatic, aromatic, or alicyclic aldehydes or ketones. Suitable aldehydes and ketones may also contain substituents such as alkoxy, hydroxy, mercapto, nitro or halogen groups. Examples of suitable aldehydes are formaldehyde, phosgene, chloroformaldehyde, bromoformaldehyde, acetaldehyde, benzaldehyde, 2-ethylhexylaldehyde, butyraldehyde, capryl aldehyde, acryl aldehyde, crotonaldehyde, vinylacetaldehyde, phenylacetaldehyde, nitrobenzaldehyde, furfural and chloral. Examples of suitable ketones are acetone, methylethyl ketone, methylhexyl ketone, dihexyl ketone, dioctyl ketone, dinonyl ketone, and didecyl ketone.

Amines which may be employed in the practice of the present invention are the $C_8$ to $C_{100}$, preferably $C_8$ to $C_{40}$, primary or secondary amines, with secondary amines being most preferred. Examples of suitable amines are dihexylamine, dioctylamine, ditallowamine, dinonylamine, didodecylamine, dihexadecylamine, hexadecylamine, octadecylamine, dicyclohexylamine, diethanol amine, 2-tertbutyl amino ethanol, N-ethyl-n-butyl amine, and N-methyl-n-octadecyl amine.

The typical 2-mercaptobenzothiazole derivative reaction product of the invention has the following general formula:

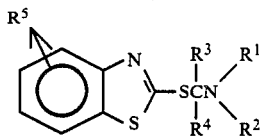

wherein $R^1$ is hydrogen or a radical derived from a substituted or unsubstituted aliphatic or alicyclic compound (i.e., a nonaromatic radical), preferably hydrogen or an unsubstituted alkyl, alkenyl or alkynyl radical, and most preferably an unsubstituted alkyl or alkenyl radical, with the total amount of carbon atoms of $R^1$ being from about 8 to about 100; preferably from about 8 to about 40; and wherein $R^2$ is hydrogen or a radical derived from a substituted or unsubstituted aliphatic or alicyclic compound (i.e., a nonaromatic radical), preferably an unsubstituted alkyl, alkenyl or alkynyl radical, and most preferably an unsubstituted alkyl or alkenyl radical, with the total amount of carbon atoms of $R^2$ being from about 8 to about 100; preferably from about 8 to about 40; and wherein $R^3$ and $R^4$ are the same or different and are hydrogen or an organic radical, preferably hydrogen or an organic radical derived from an aliphatic, alicyclic or aromatic compound, more preferably hydrogen or an unsubstituted or substituted alkyl, aryl, arylalkyl, alkyloxy, aryloxy, arylalkyloxy, alkenyl, alkenyloxy, alkynyl, alkynyloxy, or arylalkenyl radical, with the total number of carbon atoms of $R^3$ and $R^4$ independently being from 0 to about 20, preferably from 0 to about 10, and most preferably with $R^3$ and $R^4$ being hydrogen; and wherein $R^5$ is hydrogen or one or more organic substituents located on the benzene ring, with hydrogen being preferred.

Lubricating compositions which may contain the additive of the invention include substantially all oleaginous materials such as lubricating oils or greases derived from mineral or synthetic oil or mixtures thereof. Lubricating oils may be of the naphthenic or paraffinic types, with mineral and synthetic oil of any suitable lubricating viscosity useful for the purposes of the present invention. In the case of greases, substantially any grease, e.g., metal soap grease, is improved in respect to its anti-wear properties and extreme pressure characteristics by the use of the additive of the invention. The preferred oleaginous materials are lubricating oils for use in gasoline powered internal combustion engines, i.e., motor oils.

The 2-mercaptobenzothiazole derivative reaction product of the invention is incorporated into the lubricating oil or grease by blending or mixing, by any means, in a sufficient amount to enhance the extreme pressure anti-wear characteristics of the composition, as measured by means known to those skilled in the art, such as by ASTM Falex Test Method D2670-67 (reapproved 1977), herein incorporated by reference. The concentration of additive which will yield optimum results will depend upon the particular additive chosen and the particular oleaginous material into which it is introduced. The lubricating composition is provided with at least about 0.01 weight percent, preferably from about 0.25 to about 15 weight percent and most preferably from about 0.5 to about 4 weight percent of the thiazole derivative reaction product based upon the total amount of the oleaginous material and thiazole derivative reaction product.

The lubricating composition of the invention may also comprise other additives, such as corrosion inhibitors and antioxidants.

Examples of 2-mercaptobenzothiazole reaction products suitable for use in this invention for enhancing the extreme pressure, anti-wear property of lubricating compositions follow:

EXAMPLE 1

A preferred di-substituted aminomethyl derivative of 2-mercaptobenzothiazole is prepared by placing 206.0 grams of dioctadecylamine (Armeen 2HT), 66.9 grams of 2-mercaptobenzothiazole, 12.6 grams of paraformaldehyde, and 600 milliliters (ml) of toluene into a round-bottomed flask equipped with a Dean-Stark apparatus. The contents of the flask are stirred while heating to reflux, and water and toluene are co-distilled from the reaction mixture. After approximately 2 hours, 7.7 ml. of water are collected in the Dean-Stark receiver and the reaction is complete. Toluene is then vacuum-distilled from the product, which contains about 9.1 weight percent sulfur and has the formula:

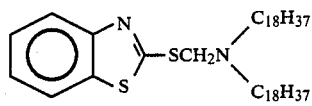

EXAMPLE 2

The preparation of a second of the preferred products is carried out by placing 643.2 grams of octadecenylamine (Armeen TD), 401.4 grams of 2-mercaptobenzothiazole, 75.6 grams of paraformaldehyde, and 1950 ml. of toluene into a round-bottomed flask equipped with a Dean-Stark apparatus. The contents of the flask are stirred while heating to reflux and water and toluene are co-distilled from the reaction mixture. After approximately 2 hours, the reaction is complete and about 47 ml. of water have been collected in the Dean-Stark receiver. The product contains about 12 weight percent of sulfur and has the formula:

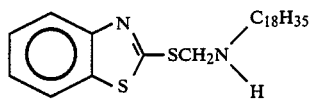

EXAMPLES 3 TO 6

Examples 3 and 4 are prepared by blending the 2-mercaptobenzothiazole derivative reaction products of Examples 1 and 2 into a 450 neutral oil at a treatment concentration to provide a 0.01645 molar solution (approximately 2.25 weight percent). Example 5 is prepared by blending 2.25 weight percent of a zinc dialkyldithiophosphate (a commercially available anti-wear additive sold by Amoco under the designation "Amoco 196") into a 450 neutral oil. These blends are then analyzed for anti-wear performance in comparison to a 450 neutral oil without an additive (Example 6) using the ASTM Falex Test Method D2670-67 (reapproved 1977). The Falex testing results for each example are listed below in Table 1 for the maximum load applied. The maximum loads listed for Examples 3 and 4 were recorded without the pin ever breaking, while the maximum load for Examples 5 and 6 were recorded immediately prior to the pin breaking. The higher the load a composition withstands, the better the anti-wear protection properties for that particular composition.

TABLE 1

| Example No. | Maximum Load |
|---|---|
| 3 | 3,500 inch pounds |
| 4 | 3,000 inch pounds |
| 5 | 1,250 inch pounds |
| 6 | 650 inch pounds |

As can be seen from the above Falex test results, lubricating compositions containing the 2-mercaptobenzothiazole derivative anti-wear additives of the invention (Examples 3 and 4) tolerate much higher loadings without pin failure than either the blank composition of Example 6 or the other anti-wear additive of Example 5. The data show that, at the 2.25 weight percent level, the preferred additives of the invention enhance the anti-wear protection of the 450 neutral oil of Example 6 by a factor of at least about 4.6 and are superior to the conventional zinc dialkyldithiophosphate of Example 5 by a factor of at least about 2.4.

While particular emodiments of the invention have been described, it will be understood that the invention is not limited thereto since many obvious modifications can be made. It is intended to include within this invention any such modifications as will fall within the scope of the appended claims.

I claim:

1. A method for enhancing the extreme pressure anti-wear characteristics of a lubricating composition comprising an oleaginous material, which method comprises admixing into said lubricating composition an extreme pressure enhancing amount of an anti-wear additive, said additive being the reaction product of (1) 2-mercaptobenzothiozole, (2) a carbonyl-containing compound selected from the group consisting of aliphatic, aromatic or alicyclic aldehydes and ketones having between 2 and 20 carbon atoms, and (3) a nitrogen-containing compound selected from the group consisting of primary and secondary amines having between 8 and 40 carbon atoms, said reaction product being soluble in said oleaginous material at a concentration of at least 2.25 percent.

2. The method of claim 1 wherein said amine is selected from the group consisting of primary and secondary aliphatic and alicyclic amines and wherein the 2-mercaptobenzothiazole, carbonyl-containing compound, and amine are reacted in a 1:1:1 molar ratio.

3. The method of claim 2 wherein the amine is a dialkyl or dicycloalkyl secondary amine.

4. The method of claim 1 wherein the carbonyl-containing compound comprises substituents selected from the group consisting of alkoxy, hydroxy, mercapto, nitro, and halogen groups.

5. The method of claim 1 wherein the carbonyl-containing compound is an aldehyde selected from the group consisting of acetaldehyde, benzaldehyde, 2-ethylhexylaldehyde, butyraldehyde, capryl aldehyde, acryl aldehyde, crotonaldehyde, vinylacetaldehyde, phenylacetaldehyde, nitrobenzaldehyde, furfural, and chloral.

6. The method of claim 1 wherein the amine is selected from the group consisting of dihexylamine, dioctylamine, ditallowamine, dinonylamine, didodecylamine, dihexadecylamine, hexadecylamine, octadecylamine, dicyclohexylamine, and N-methyl-n-octadecylamine.

7. The method of claim 1 wherein the carbonyl-containing compound is a ketone selected from the group consisting of acetone, methylethyl ketone, methylhexyl ketone, dihexyl ketone, dioctyl ketone, dinonyl ketone, and didecyl ketone.

8. A method for enhancing the extreme pressure anti-wear characteristics of a lubricating composition comprising an oleaginous material, which comprises admixing into said lubricating composition an extreme pressure anti-wear enhancing amount of an ashless and metals-free compound of the formula:

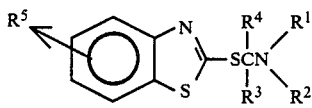

wherein:
R$^1$ and R$^2$ are the same or different substituents selected from the group consisting of hydrogen and metals-free, substituted or unsubstituted alkyl, alkenyl, alkenyloxy, alkynyl, alkynyloxy, and cyclic hydrocarbon radicals, and heteroatom-substituted hydrocarbyl radicals wherein the heteroatoms are selected from the class consisting of oxygen, sulfur, and nitrogen atoms provided that R$^1$ and R$^2$ have a total of between about 8 and about 40 carbon atoms and are not both hydrogen;
R$^3$ and R$^4$ are the same or different substituents selected from the group consisting of hydrogen and metal-free, substituted or unsubstituted alkyl, aryl, arylalkyl, alkyloxy, aryloxy, arylalkyloxy, alkenyl, alkenyloxy, alkynyl, alkynyloxy, arylalkenyl, and cyclic hydrocarbon radicals, and heteroatom-substituted hydrocarbyl radicals wherein the heteroatoms are selected from the group consisting of oxygen, sulfur and nitrogen atoms provided that R$^3$ and R$^4$ have a total of between about 8 and 20 carbon atoms and are not both hydrogen; and
R$^5$ is hydrogen or one or more organic substituents located on the benzene ring.

9. The method of claim 8 wherein R$^3$ is hydrogen.

10. The method of claim 8 wherein R$^3$ and R$^4$ independently contain between 0 and 10 carbon atoms.

11. The method of claim 8 wherein R$^1$ and R$^2$ independently contain between about 4 and about 50 carbon atoms.

12. The method of claim 1 wherein the oleaginous material is selected from the group consisting of lubricating oils or greases derived from mineral or synthetic oils.

13. The method of claim 1 wherein the oleaginous material comprises lubricating oils for use in gasoline-powered internal combustion engines.

14. The method of claim 1 wherein the extreme pressure enhancing amount is at least about 2.25 weight percent of the total amount of the compound and oleaginous material.

15. The method of claim 1 wherein said extreme pressure anti-wear enhancing reaction product is metals-free and ashless.

16. A method for enhancing the extreme pressure anti-wear characteristics of a lubricating composition comprising an oleaginous material, which method comprises admixing into said lubricating composition an extreme pressure, anti-wear enhancing amount of an ashless and metals-free additive having the formula:

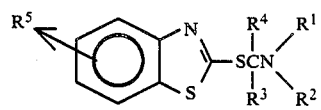

wherein R$^1$ and R$^2$ are independently organic radicals or hydrogen, provided that both R$^1$ and R$^2$ are not simultaneously hydrogen, and further provided that the total number of carbon atoms in R$^1$ and R$^2$ is between 8 and 40, R$^3$ and R$^4$ are independently organic radicals, bromine, chlorine or hydrogen, provided that at least one of R$^3$ and R$^4$ is an organic radical, and further provided that the total number of carbon atoms in R$^3$ and R$^4$ is between 1 and 20, and R$^5$ is selected from the group consisting of hydrogen and organic radicals, said additive being soluble in 450 neutral oil at a concentration of at least 2.25 weight percent.

17. A lubricating composition comprising an oleaginous composition and an extreme pressure anti-wear enhancing amount of the reaction product of (1) 2-mercaptobenzothiazol, (2) a carbonyl-containing compound selected from the group consisting of aliphatic, aromatic or alicyclic aldehydes and ketones having between 2 and 20 carbon atoms, and (3) a nitrogen-containing compound selected from the group consisting of primary and secondary amines having between 8 and 40 carbon atoms, said reaction product being soluble in 450 neutral oil at a concentration of at least 2.25 weight percent.

18. The composition of claim 17 wherein the 2-mercaptobenzothiazole, carbonyl-containing compound and amine are reacted in a 1:1:1 molar ratio.

19. The composition of claim 17 wherein the carbonyl-containing compound has one or more substituents selected from the group consisting of alkoxy, hydroxy, mercapto, nitrogen, and halogen groups.

20. The composition of claim 18 wherein said amine is a secondary amine selected from the group consisting of dihexyl amine, dioctyl amine, ditallow amine, dinonyl amine, didodecyl amine, dihexadecyl amine and dicyclohexyl amine.

21. A lubricating composition comprising an oleaginous material and an ashless and metals-free, extreme pressure, anti-wear additive of the formula:

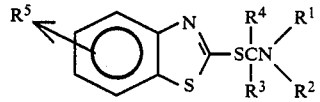

wherein:
R$^1$ and R$^2$ are the same or different substituents selected from the group consisting of hydrogen and metals-free, substituted or unsubstituted alkyl, alkenyl, alkenyloxy, alkynyl, alkynyloxy, and cyclic hydrocarbon radicals, and heteroatom-substituted hydrocarbyl radicals wherein the heteroatoms are selected from the class consisting of oxygen, sulfur, and nitrogen atoms provided that $R^1$ and $R^2$ have a total of between about 8 and about 40 carbon atoms and are not both hydrogen;

$R^3$ and $R^4$ are the same or different substituents selected from the group consisting of hydrogen and metal-free, substituted or unsubstituted alkyl, aryl, arylalkyl, alkyloxy, aryloxy, arylalkyloxy, alkenyl, alkenyloxy, alkynyl, alkynyloxy, arylalkenyl, and cyclic hydrocarbon radicals, and heteroatom-substituted hydrocarbyl radicals wherein the heteroatoms are selected from the group consisting of oxygen, sulfur and nitrogen atoms provided that $R^3$ and $R^4$ have a total of between about 8 and 20 carbon atoms and are not both hydrogen; and $R^5$ is hydrogen or one or more organic substituents located on the benzene ring.

22. A lubricating composition comprising an oleaginous material and an ashless and metals-free, extreme pressure, anti-wear additive, said additive being a reaction product of (1) 2-mercaptobenzothiazole, (2) a carbonyl-containing compound selected from the group consisting of aliphatic, aromatic or alicyclic adehydes and ketones having 2 to 20 carbon atoms, and (3) a nitrogen-containing compound comprising a primary or secondary amine.

23. The lubricating composition of claim 22 wherein the amine is an aliphatic or cycloaliphatic amine and wherein the 2-mercaptobenzothiazole, carbonyl-containing compound and amine are reacted in a 1:1:1 molar ratio.

24. The lubricating composition of claim 22 wherein the carbonyl-containing compound has one or more substituents selected from the group consisting of alkoxy, hydroxy, mercapto, nitro and halogen groups.

25. The lubricating composition of claim 22 wherein the carbonyl-containing compound is an aldehyde selected from the group consisting of phosgene, acetaldehyde, benzaldehyde, 2-ethylhexyl aldehyde, butyraldehyde, capryl aldehyde, acryl aldehyde, croton aldehyde, vinyl acetaldehyde, phenyl acetaldehyde, nitro benzaldehyde, furfural and chloral.

26. The lubricating composition of claim 22 wherein the carbonyl-containing compound is a ketone selected from the group consisting of acetone, methylethyl ketone, methylhexyl ketone, dihexyl ketone, dioctyl ketone, dinonyl ketone and di decyl ketone.

27. The lubricating composition of claim 23 wherein the carbonyl-containing compound contains between 2 and about 10 carbon atoms.

28. The lubricating composition of claim 22 wherein the amine contains between about 8 and about 40 carbon atoms.

29. The lubricating composition of claim 22 wherein the amine is selected from the group consisting of dihexyl amine, dioctyl amine, ditallow amine, dinonyl amine, didodecyl amine, dihexadecyl amine, hexadecyl amine, octadecyl amine, dicyclohexyl amine and N-methyl-n-octadecyl amine.

30. The lubricating composition of claim 22 wherein the amine is a dialkyl or dicycloalkyl secondary amine containing between about 8 and about 40 carbon atoms.

* * * * *

UNITED STATES PATENT AND TRADEMARK OFFICE
CERTIFICATE OF CORRECTION

PATENT NO. : 4,764,298
DATED : 08/16/88
INVENTOR(S) : Croudace

It is certified that error appears in the above-identified patent and that said Letters Patent is hereby corrected as shown below:

Column 7, claim 8, line 17, between "which" and "comprises" insert -- method --

Column 7, claim 8, line 34, delete "class" and insert therefor -- group --.

Column 7, claim 12, line 58, delete "1" and insert therefor -- 8 --.

Column 7, claim 13, line 62, delete "1" and insert therefor -- 8 --.

Column 7, claim 14, line 65, delete "1" and insert therefor -- 8 --.

Signed and Sealed this

Ninth Day of May, 1989

Attest:

DONALD J. QUIGG

*Attesting Officer*   *Commissioner of Patents and Trademarks*